United States Patent
Griffin

(10) Patent No.: US 12,367,894 B2
(45) Date of Patent: Jul. 22, 2025

(54) MULTIDIMENSIONAL MENTAL STATE PREDICTION

(71) Applicant: Insight Direct USA, Inc., Tempe, AZ (US)

(72) Inventor: Michael Griffin, Wayland, MA (US)

(73) Assignee: Insight Direct USA, Inc., Chandler, AZ (US)

(*) Notice: Subject to any disclaimer, the term of this patent is extended or adjusted under 35 U.S.C. 154(b) by 390 days.

(21) Appl. No.: 17/951,940

(22) Filed: Sep. 23, 2022

(65) Prior Publication Data

US 2023/0178098 A1  Jun. 8, 2023

Related U.S. Application Data

(60) Provisional application No. 63/405,725, filed on Sep. 12, 2022, provisional application No. 63/405,726, (Continued)

(51) Int. Cl.
*G10L 25/63* (2013.01)
*A61B 5/00* (2006.01)
(Continued)

(52) U.S. Cl.
CPC .............. *G10L 25/63* (2013.01); *A61B 5/165* (2013.01); *A61B 5/4803* (2013.01); (Continued)

(58) Field of Classification Search
CPC ....... G10L 25/63; A61B 5/165; A61B 5/4803; A61B 5/7275; A61B 5/0077; (Continued)

(56) References Cited

U.S. PATENT DOCUMENTS

| 2014/0093849 A1* | 4/2014 | Ahn | G06N 3/008 434/236 |
| 2016/0358085 A1* | 12/2016 | Abadi | G16H 50/70 |

(Continued)

OTHER PUBLICATIONS

Zhang, Hanzhong, Jibin Yin, and Xiangliang Zhang. "The Study of a Five-Dimensional Emotional Model for Facial Emotion Recognition." Mobile Information Systems 2020.1 (2020): 8860608. (Year: 2020).*

*Primary Examiner* — Henok Shiferaw
*Assistant Examiner* — Dion J Satcher
(74) *Attorney, Agent, or Firm* — Kinney & Lange, P.A.

(57) ABSTRACT

A method of predicting mental state includes extracting image data, audio data, and semantic text data from video data, where the video data portrays a first individual. The method further includes analyzing the image data to identify a first feature set, analyzing the audio data to identify a second feature set, analyzing the semantic text data to identify a third feature set, and predicting a mental state for the individual based on the first feature set, the second feature set, the third feature set, and a multidimensional mental state model. The predicted mental state is output. The multidimensional mental state model includes a first dimension, a second dimension, and a third dimension. The first dimension corresponds to a first aspect of mental state, the second dimension corresponds to a second aspect of mental state, and the third dimension corresponds to a third aspect of mental state.

10 Claims, 5 Drawing Sheets

Related U.S. Application Data filed on Sep. 12, 2022, provisional application No. 63/286,844, filed on Dec. 7, 2021.

(51) Int. Cl.
*A61B 5/16* (2006.01)
*G06F 40/30* (2020.01)
*G06V 10/22* (2022.01)
*G06V 10/44* (2022.01)
*G06V 10/70* (2022.01)
*G06V 20/40* (2022.01)
*G06V 40/16* (2022.01)
*G06V 40/20* (2022.01)

(52) U.S. Cl.
CPC ............ *A61B 5/7275* (2013.01); *G06F 40/30* (2020.01); *G06V 10/22* (2022.01); *G06V 10/44* (2022.01); *G06V 10/70* (2022.01); *G06V 20/41* (2022.01); *G06V 20/46* (2022.01); *G06V 40/171* (2022.01); *G06V 40/20* (2022.01)

(58) Field of Classification Search
CPC ...... A61B 5/7267; G06F 40/30; G06V 10/22; G06V 10/44; G06V 10/70; G06V 20/41; G06V 20/46; G06V 40/171; G06V 40/20; G06V 40/28; G06V 10/764
See application file for complete search history.

(56) References Cited

U.S. PATENT DOCUMENTS

| | | | |
|---|---|---|---|
| 2019/0012599 A1* | 1/2019 | el Kaliouby | G06N 3/084 |
| 2020/0138356 A1* | 5/2020 | Sharon | A61B 5/0205 |
| 2021/0000404 A1* | 1/2021 | Wang | A61B 5/7275 |
| 2021/0191506 A1* | 6/2021 | Wang | G06F 3/017 |
| 2021/0287697 A1* | 9/2021 | Marti | G10L 25/63 |
| 2021/0352380 A1* | 11/2021 | Duncan | H04N 21/4884 |
| 2022/0270636 A1* | 8/2022 | Tao | G06F 40/284 |

\* cited by examiner

MULTIDIMENSIONAL MENTAL STATE PREDICTION

CROSS-REFERENCE TO RELATED APPLICATION(S)

This application claims the benefit of U.S. Provisional Application No. 63/286,844 filed Dec. 7, 2021 for "MACHINE LEARNING METHOD TO QUANTIFY PRESENT STATE-OF-MIND AND PREDICT FUTURE STATE-OF-MIND OF ONE OR MORE INDIVIDUALS BASED ON VIDEO IMAGES OF THOSE INDIVIDUALS" by M. Griffin, H. Kotvis, K. Lumb, K. Poulson, and J. Miner, the disclosure of which is incorporated in its entirety by reference herein; of U.S. Provisional Application No. 63/405,726 filed Sep. 12, 2022 for "MULTIDIMENSIONAL MENTAL STATE PREDICTION" by M. Griffin, the disclosure of which is incorporated in its entirety by reference herein; and of U.S. Provisional Application No. 63/405,725 filed Sep. 12, 2022 for "GROUP MULTIDIMENSIONAL MENTAL STATE PREDICTION" by M. Griffin, the disclosure of which is also incorporated in its entirety by reference herein.

BACKGROUND

The present disclosure relates to mental state prediction and, more particularly, systems and methods for predicting mental state using video data.

Individuals convey information in multiple ways, including verbal and non-verbal means. In conversational or social interactions, interpreting verbal and non-verbal information simultaneously and in real-time can be difficult. Further, some individuals have impairments or disabilities that can significantly increase the difficulty of interpreting verbal and/or non-verbal information.

SUMMARY

An embodiment of a method of predicting mental state according to the present disclosure includes extracting image data, audio data, and semantic text data from video data, where the video data portrays a first individual. The method further includes analyzing the image data to identify a first feature set, analyzing the audio data to identify a second feature set, analyzing the semantic text data to identify a third feature set, and predicting a mental state for the individual based on the first feature set, the second feature set, the third feature set, and a multidimensional mental state model. The predicted mental state is output. The multidimensional mental state model includes a first dimension, a second dimension, and a third dimension. The first dimension corresponds to a first aspect of mental state, the second dimension corresponds to a second aspect of mental state, and the third dimension corresponds to a third aspect of mental state.

An embodiment of a system for predicting individual mental state according to the present disclosure includes a processor, a user interface, and memory. The user interface is configured to enable an operator to interact with the processor. The memory is encoded with instructions that, when executed, cause the processor to extract audio data extract image data, audio data, and semantic text data from video data, wherein a first individual is portrayed in the video data. The instructions further cause the processor to analyze the image data to identify a first feature set, analyze the audio data to identify a second feature set, analyze the semantic text data to identify a third feature set, predict a mental state for the individual based on the first feature set, the feature set, the third feature set, and a multidimensional mental state model, and to output the predicted mental state. The multidimensional mental state model includes a first dimension, a second dimension, and a third dimension, the first dimension corresponds to a first aspect of mental state, the second dimension corresponds to a second aspect of mental state, and the third dimension corresponds to a third aspect of mental state.

DETAILED DESCRIPTION

Figure 1:
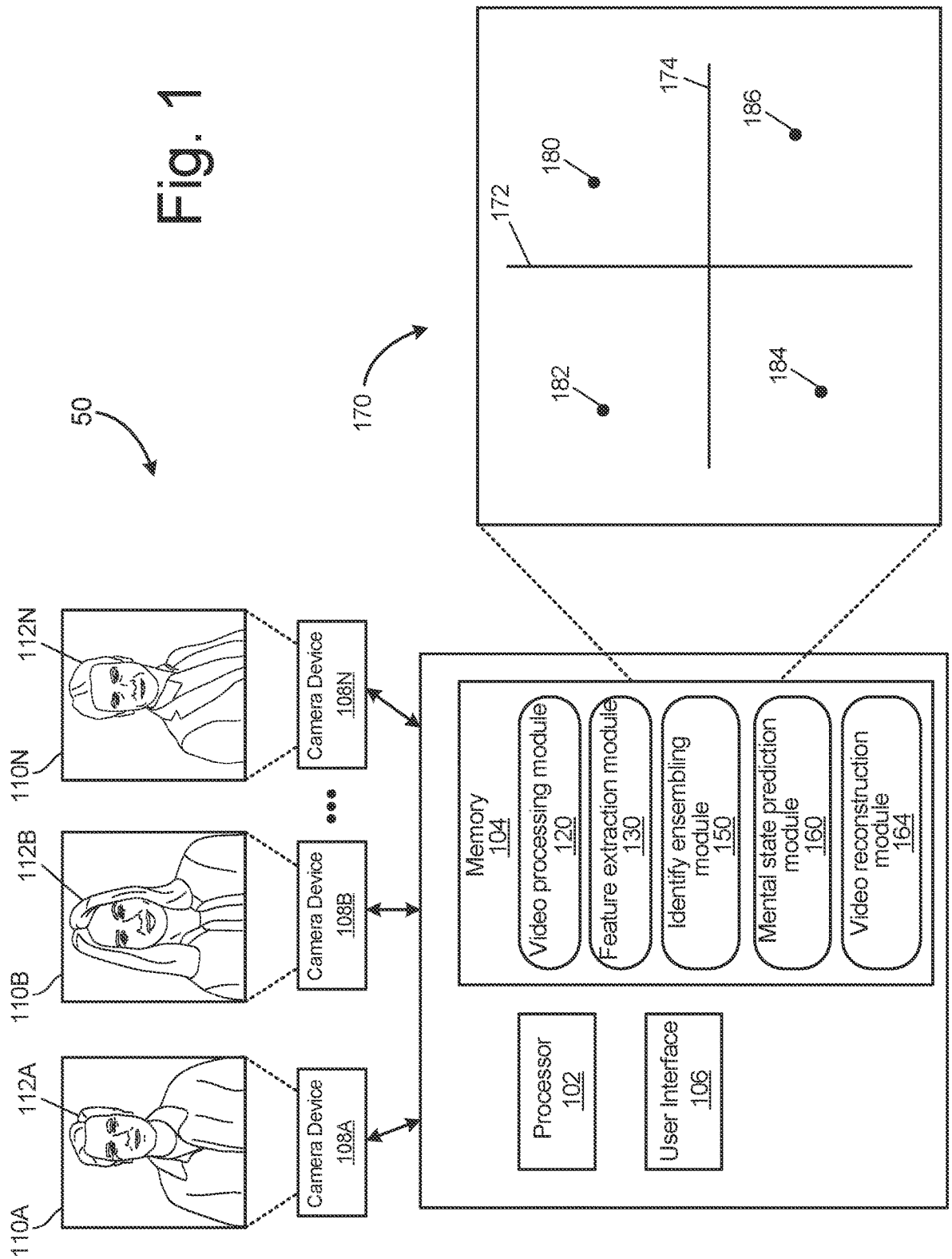
FIG. 1 is a schematic diagram of an example of a system for classifying mental state.

The present disclosure relates to systems and method for predicting state of mind of an individual captured in video data. Specifically, the present disclosure relates to methods and systems for predicting mental state according to a multidimensional mental state model. As will be explained in more detail subsequently, multidimensional mental state models assign different aspects of mental state to different dimensions of the model and thereby significantly improve the resolution and accuracy of mental state predictions as compared to existing models of mental state.

As used herein, "mental state" refers to the attitude, mood, and/or emotion of an individual. The mental state of an individual can be significantly more complex than, for example, an emotion of the individual. Existing methods can use video data to identify discrete emotions and are not capable of identifying more complex mental states. As will be explained in substantially more detail subsequently, the multidimensional mental state models described herein advantageously are able to distinguish and identify an individual's mental state, as opposed to simply identifying the individual's emotion. For example, existing methods focused on emotion may limited to simple emotional states such as "happy," "sad," "neutral," or "afraid," while a multidimensional mental state model according to the present disclosure can be used to identify more complex mental states, such as "bored," "satisfied," "sleepy," or "content" in addition to the emotional states identifiable by simpler existing methods.

Further, the multidimensional mental state models described herein allow for mental state to be determined based on the extent to which an individual is experiencing various mental state components that contribute to an overall mental state. For example, it is possible for an individual to be simultaneously or substantially simultaneously experiencing two or more emotions, attitudes, and/or moods in varying degrees. Each emotion, attitude, and/or mood can be described by a dimension of the multidimensional mental state model, allowing the individual's overall mental state to be determined with significantly more accuracy and granularity than existing methods that use a single emotion, attitude, and/or mood to describe mental state.

Current methods of estimating individual emotion or attitude also specialize in extremely narrow use cases (e.g., analyzing the alertness of automobile drivers or eye-tracking to gauge a person's attention level). These existing methods extract only a small fraction of the emotion information contained in the video feed and do not attempt to analyze more than one individual at a time. Advantageously, the use of a multidimensional mental state model rather than a simpler, existing emotion model allows the systems and methods disclosed herein to be applied to a wide variety of applications and use cases, reducing the need for the development of use-case specific models to understand mental state.

The present disclosure also provides systems and methods for predicting mental state using data contained in a video file or video stream. Image, audio, and text data can be extracted from video data and used to determine various aspects of the mental state of an individual portrayed in the video data. Notably, different dimensions of the individual's mental state, according to the multidimensional mental state model, can be determined using different elements of the video data (e.g., image, audio, and/or text data).

Further, the present disclosure provides methods that can be performed using computer-implemented machine learning models to provide real-time analysis of mental state predictions. Advantageously, this allows the mental state predictions to be presented in real-time or substantially real-time, enabling other conversation participants to better understand the individual's mental state as the conversation is occurring. Notably, the real-time mental state predictions enabled by computer-implemented machine learning models enable the systems and methods of the present disclosure to improve accessibility for individuals with hearing, vision, and/or perception impairments. For example, real-time mental state predictions according to the present disclosure can be used to present information conveyed by body language and/or vocal tone to a person with sight and/or hearing impairments, respectively, significantly improving the ability of the person with the impairment or impairments to participate in conversations and other social interactions.

FIG. 1 is a schematic view of mental state classification system 50, which is a system for generating mental state information. Mental state classification system 50 includes mental state classifier 100, which includes processor 102, memory 104, and user interface 106 and is connected to camera devices 108A-N. Camera devices 108A-N capture video data 110A-N of individuals 112A-N. Memory 104 includes video processing module 120, feature extraction module 130, identity ensembling module 150, mental state prediction module 160, and video reconstruction module 164. Memory 104 also stores multidimensional mental state model 170, which includes first dimension 172, second dimension 174, first point 180, second point 182, third point 184, and fourth point 186.

Processor 102 can execute software, applications, and/or programs stored on memory 104. Examples of processor 102 can include one or more of a processor, a microprocessor, a controller, a digital signal processor (DSP), an application specific integrated circuit (ASIC), a field-programmable gate array (FPGA), or other equivalent discrete or integrated logic circuitry. Processor 102 can be entirely or partially mounted on one or more circuit boards.

Memory 104 is configured to store information and, in some examples, can be described as a computer-readable storage medium. Memory 104, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 104 is a temporary memory. As used herein, a temporary memory refers to a memory having a primary purpose that is not long-term storage. Memory 104, in some examples, is described as volatile memory. As used herein, a volatile memory refers to a memory that that the memory does not maintain stored contents when power to the memory 104 is turned off. Examples of volatile memories can include random access memories (RAM), dynamic random access memories (DRAM), static random access memories (SRAM), and other forms of volatile memories. In some examples, memory 104 is used to store program instructions for execution by processor 102. Memory 104, in one example, is used by software or applications running on the mental state classifier (e.g., by a computer-implemented machine learning model or a data processing module) to temporarily store information during program execution.

Memory 104, in some examples, also includes one or more computer-readable storage media. The memory can be configured to store larger amounts of information than volatile memory. The memory can further be configured for long-term storage of information. In some examples, the memory includes non-volatile storage elements. Examples of such non-volatile storage elements can include, for example, magnetic hard discs, optical discs, floppy discs, flash memories, or forms of electrically programmable memories (EPROM) or electrically erasable and programmable (EEPROM) memories.

User interface 106 is an input and/or output device and enables an operator to control operation of mental state classifier 100. For example, user interface 106 can be configured to receive inputs from an operator and/or provide outputs regarding predicted individual mental state. User interface 106 can include one or more of a sound card, a video graphics card, a speaker, a display device (such as a liquid crystal display (LCD), a light emitting diode (LED) display, an organic light emitting diode (OLED) display, etc.), a touchscreen, a keyboard, a mouse, a joystick, or other type of device for facilitating input and/or output of information in a form understandable to users and/or machines.

Mental state classifier 100 is configured to perform one or more methods described herein and/or implement one or more of the mental state classification modules described herein. Mental state classifier 100 can accept data from and/or can be operably connected to an audiovisual data stream and/or an audiovisual data file. Mental state classifier 100 can use data from an audiovisual data stream and/or an audiovisual data file to determine mental state information. More generally, mental state classifier 100 is configured to perform any of the functions attributed herein to a mental state classifier, including receiving an output from any source referenced herein, detecting any condition or event referenced herein, and generating and providing data and information as referenced herein.

Mental state classifier 100 can be a discrete assembly or be formed by one or more devices capable of individually or collectively implementing functionalities and generating and outputting data as discussed herein. In some examples, mental state classifier 100 can be implemented as a plurality of discrete circuitry subassemblies. In some examples, mental state classifier 100 can include or be implemented at least in part as a smartphone or tablet, among other options. In some examples, mental state classifier 100 and/or user interface 106 of mental state classifier 100 can include and/or be implemented as downloadable software in the form of a mobile application. The mobile application can be implemented on a computing device, such as a personal computer, tablet, or smartphone, among other suitable devices. Mental state classifier 100 can be considered to form a single computing device even when distributed across multiple component devices.

Camera devices 108A-N are capable of capturing video data 110A-N of one or more individuals 112A-N. In the depicted example, each camera device 108A-N captures video data 110A-N of a single individual 112A-N. In other examples, each camera device 108A-N captures video data 110A-N of multiple individuals 112A-N. Each camera device 108A-N is configured to be able to communicate with mental state classifier 100 and mental state classifier 100 is configured to communicate with each camera device 108A-N. Camera devices 108A-N can be, for example, a video camera, a webcam, or another suitable source for obtaining video data 110A-N. Camera devices 108A-N can be controlled by mental state classifier 100 or by another suitable video device. Video data 110A-N are audiovisual data feeds portraying individuals 112A-N. Video data 110A-N can be stored to memory 104 for use with one or more methods described herein or can be stored to another storage media and recalled to memory 104 for use with one or more methods described herein.

Although mental state classification system 50 is depicted as only including three camera devices 108A-N, mental state classification system 50 can include any number of camera devices 108A-N. Each additional camera device 108A-N can capture video data 110A-N portraying another individual 110A-N. Similarly, although each of video data 110A-N is depicted as portraying a single individual 110A-N, in other examples each of video data 110A-N can depict two or more individuals 110A-N.

Video processing module 120 includes one or more programs for processing video data 110A-N. For example, video processing module 120 can include one or more programs for extracting image data, audio data, and semantic text data from video data 110A-N. As used herein, "image data" refers to the portion of video data 110A-N that is a series of still images, "audio data" refers to the sound data stored in video data 110A-N, and semantic text data refers to data that represents spoken words, phrases, sentences, and other sounds produced by the individual as readable text.

Feature extraction module 130 includes one or more programs for classifying the image data, audio data, and semantic text data extracted by video processing module 120. Feature extraction module 130 can include one or more programs for extracting classifiable features from the image data, audio data, and/or semantic text data. In some examples, feature extraction module 130 can include one or more computer-implemented machine learning models for extracting classifiable features from the image data, audio data, and/or semantic text data. The features extracted by feature extraction module 130 are capable of being classified to predict an individual's mental state and/or to identify the individual.

Identity ensembling module 150 includes one or more programs for identifying an individual portrayed in video data based on the features extracted by feature extraction module 130. In some examples, identity ensembling module 150 can use one or more computer-implemented machine learning models to identify an individual portrayed in video data.

Mental state prediction module 160 includes one or more programs for predicting the mental state of an individual portrayed in video data based on the features extracted by feature extraction module 130. In some examples, mental state prediction module 160 can use one or more computer-implemented machine learning models to predict the mental state of an individual portrayed in video data.

Video reconstruction module 164 includes one or more programs for reconstructing enhanced video data. The enhanced video data includes the image data and audio data extracted from the video data processed by video processing module 120, but is enhanced with additional images, audio, and/or text based on the information generated by identity ensembling module 150 and/or mental state prediction module 160. The enhanced video produced by video reconstruction module 164 can be output by user interface 106 to enable a user to quickly understand the information generated by ensembling module 150 and/or mental state prediction module 160 while watching only video feed of the individual.

Memory 104 also stores multidimensional mental state model 170, which is a model for classifying the mental state of an individual 112A-N portrayed in video data 110A-N. Multidimensional mental state model 170 includes first dimension 172 and second dimension 174. As used herein, a "multidimensional mental state model" refers to a model of mental state that assigns different aspects of mental state to different dimensions of the model. Advantageously, multidimensional mental state models describe mental state more accurately than existing models of mental state. Because mental state models more accurately describe an individual's mental state, multidimensional mental state models significantly improve the resolution and accuracy of predictions of mental state as compared to existing models, including single-dimensional models of mental state.

Referring to multidimensional mental state model 170, first dimension 172 can represent an intensity of an individual's mental state and second dimension 174 can represent a pleasantness of the individual's mental state. Different mental states can be described by different combinations of values in first dimension 172 and second dimension 174. For example, each quadrant of multidimensional mental state model 170 can represent a different mental state or different subregions of multidimensional mental state model 170 (including subregions entirely within and/or extending across quadrants of multidimensional mental state model 170) can represent different mental states.

Additionally and/or alternatively, the dimensions of multidimensional mental state model 170 can represent mental state by describing aspects of information communicated by the individual (i.e., in the image data, audio data, and/or semantic text data for an individual), such as the relative importance of the information the individual is conveying information, the positivity of the information the individual is conveying, and/or the subject of the conversation in which the individual is participating (e.g., whether the subject is administrative, technical, etc.), among other options. The importance of the information the individual is conveying can be assessed based on, for example, a task or job the individual is performing.

In other examples, each of first dimension 172 and second dimension 174 can represent separate mental states. For example, first dimension 172 can represent a first mental state, such as confusion, and second dimension 174 can represent a second mental state, such as calmness. Various regions, such as quadrants, of multidimensional mental state model 170 can represent different combinations of confusion and calmness, with each region representing a discrete overall mental state. Simultaneously monitoring confusion and calmness can allow, for example, a measurement of how well the first individual and the second individual are retaining information as audience members to a presentation or lecture. More specifically, a quadrant with positive confusion and calmness values can represent an overall "confused and attentive" mental state; a quadrant with negative confusion and calmness values can represent an overall "comprehending and attentive" mental state; a quadrant with negative confusion and negative calmness can represent an overall "comprehending and inattentive" mental state; and a quadrant with positive confusion and negative calmness can represent an overall "confused and inattentive" mental state.

In other examples, the dimensions of multidimensional mental state model 170 can represent any other combination of mental states. For example, the dimensions of multidimensional mental state model can also include one or more of tiredness, sleepiness, serenity, satisfaction, calmness, relaxation, contentment, distress, frustration, anger, annoyance, tension, fear, alarm, misery, sadness, depression, gloom, boredom, astonishment, amusement, excitement, happiness, delight, gladness, pleasure, thankfulness, gratitude, confusion, smugness, deliberation, anticipation, cheer, sympathy, trust, humor, envy, melancholy, hostility, resentment, revulsion, and/or ennui. As a specific example, the multidimensional mental state model 170 can include three dimensions, where each dimension represents an intensity of a specific mental state. The three dimensions can represent intensities of, for example, frustration, fear, and excitement, respectively.

Points 180-186 represent different combinations of values along the first dimension and the second dimension of multidimensional mental state model 170. In examples where first dimension 172 and second dimension 174 represent intensity and pleasantness of an individual's mental state, respectively, point 180 corresponds to a mental state having relatively high intensity and relatively high pleasantness, such as happiness. Point 182 corresponds to a mental state having relatively high intensity and relatively low pleasantness, such as frustration or annoyance. Point 184 corresponds to a mental state having low intensity and low pleasantness, such as boredom. Point 186 corresponds to a mental state having low intensity and high pleasantness, such as relaxation.

As will be explained in further detail subsequently, multidimensional mental state models, such as multidimensional mental state model 170, more accurately describe the mental state of an individual than mental state models having only a single dimension. For example, multidimensional mental state model 170 enables the mental states of amusement, excitement, happiness, delight, gladness and pleasure to be distinguished. Existing, one-dimensional models of mental state are unable to clearly distinguish between closely related mental states. Further, multidimensional mental state models having more than two dimensions more accurately describe the mental state of an individual than mental state models having only two dimensions. For example, it is possible for an individual to be confused, envious, and sleepy simultaneously. A three-dimensional mental state model having dimensions describing each of confusion, envy, and sleepiness can more accurately describe the mental state of an individual experiencing all three mental states to varying degrees than existing representations or models of mental state. As such, the use of a multidimensional mental state model enables significantly more accurate prediction of an individual's mental state.

Mental state prediction module 160 can be used to generate values for each dimension of multidimensional mental state model 170. In some examples, mental state prediction module 160 can use different types of data (i.e., image, audio, and semantic text) can be used to generate values for each of first dimension 172 and second dimension 174. The use of different combinations of the three types of information present in video data provides further advantages and improvements to both the efficiency and accuracy of the multidimensional mental state model. More specifically, excluding different combinations of image, audio, and text data allows mental state predictions to be made using only predictive data rather than non-predictive data. For example, text data may offer significantly more insight into the importance of a particular discussion than image or audio data. The multidimensional mental state model can be configured so that only features from the text data are used to calculate the dimension associated with discussion importance, improving accuracy by disregarding non-predictive data and, consequently, improving efficiency by only requiring one type of data to calculate the dimensional value for the discussion importance dimension.

While multidimensional mental state model 170 is depicted in FIG. 1 as only including first dimension 172 and second dimension 174, additional dimensions can be added to multidimensional mental state model 170 as required for a given application and/or operational need. Adding additional dimensions to multidimensional mental state model 170 can allow nearby or similar mental states to be further distinguished, thereby improving the resolution of multidimensional mental state model 170. For example, additional dimensions describing information importance, information positivity, the subject of the information (i.e., whether the information is administrative, technical, etc.), and/or other mental states can further be used to resolve and distinguish between similar overall mental states. In examples where each dimension of the multidimensional mental state model represents a separate mental state (e.g., one or more of confusion, envy, calmness, sleepiness, etc.), the inclusion of additional dimensions can also allow for more accurate description of an individual's mental state.

In operation, mental state classifier 100 allows for the prediction of mental state based only on information communicated by an individual 112A-N in video data 110A-N captured by cameras 108A-N. Conventional methods of predicting mental state rely on complex biometric data. Collecting biometric data can require complex machines and, further, often requires physically-intrusive methods. Conversely, mental state classifier 100 allows for mental state to be predicted using only video data 110A-N, which can be collected using only cameras 108A-N and without the use of any physically-intrusive techniques.

Figure 2:
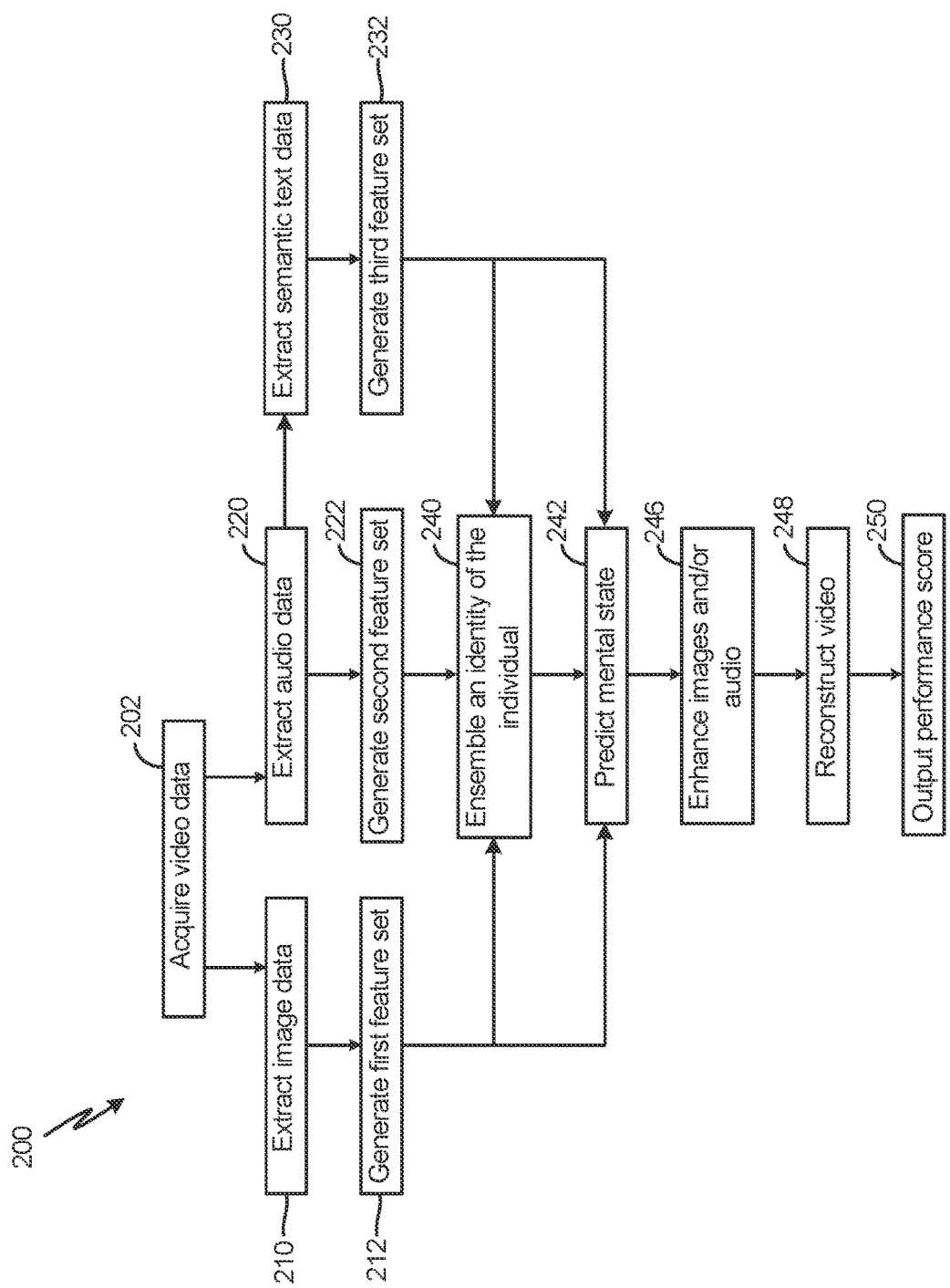
FIG. 2 is a flow diagram of an example of a method of predicting mental state.

FIG. 2 is a flow diagram of method 200, which is a method of classifying an individual's mental state. Method 200 extracts features that relate to information conveyed by an individual captured in video data and uses the extracted features to predict mental state according to a multidimensional mental state model. Specifically, method 200 includes steps 202-250 of acquiring video data (step 202), extracting image data (step 210), generating a first feature set (step 212), extracting audio data (step 220), generating a second feature set (step 222), extracting semantic text data (step 230), generating a third feature set (step 232), ensembling the individual's identity (step 240), predicting the individual's mental state (step 242), enhancing video and/or audio (step 246), reconstructing the video (step 248), and outputting the reconstructed video (step 250). Steps of method 200 are discussed herein with reference to mental state classifier 100 for explanatory purposes, but method 200 can be performed with any suitable computing device or computing devices in other examples.

In step 202, video data is acquired by processor 102 from a camera of cameras 108A-N or from another suitable video source. The video data can be delivered to mental state classifier 100 from a video source and/or mental state classifier 100 can request the video data from the video source. The video source can be any suitable source of video, such as a multimedia file or a video stream. The video stream can be, for example, a video stream acquired from a video conferencing platform. The video data can be of any length, but in some examples, the video data is sampled at pre-determined intervals for use with method 200. Method 200 can be performed for each segment of the video data and updated individual mental state information can be provided for each segment.

In step 210, processor 102 extracts images of the individual from the video acquired in step 202. The extracted images are stored to memory 104 as still images. Processor 102 can use one or more programs, such as one or more programs of video processing module 120, to extract still image data from the video data. In some examples, the image data is cropped such that only the individual's face is contained in the extracted image data.

In step 212, processor 102 generates a first feature set based on the image data of the individual extracted in step 210. Processor 102 can inspect the image data using, for example, a computer vison model for features that indicate the conveyance of information, such as hand gestures, head tilt, the presence and amount of eye contact, the amount of eye blinking, forehead wrinkling, mouth position, mouth shape, eyebrow shape, and/or eyebrow position, among other options. Processor 102 can then create one or more values that describe the information conveyed by the detected features and store the value or values to memory 104 as the first feature set. As will be explained subsequently, the first feature set generated in step 212 can be used in step 242 in combination with other feature sets generated during steps 222 and 232 of method 200 (i.e., during steps 222 and/or 232) to predict the individual's mental state. In examples where an identifier was assigned to image data in step 210, the identifier can also be assigned to the first feature set.

The features extracted in step 212 can also relate to aspects of the individual's identity, such as physical attributes of the individual, the individual's physical environment, and/or the individual's physical location, among other examples. The features that relate to the individual's identity can be stored to the first feature set for use with step 240 of method 200 and, in some examples, can be labeled such that they are distinguished from features that relate to information conveyed by the individual suitable for predicting mental state.

In some examples, step 212 is performed using one or more computer-implemented machine learning models. The machine learning model or machine learning models can be trained to identify features useful for predicting an individual's state of mind and/or determining an individual's identity.

In step 220 of method 200, processor 102 extracts individual audio from the raw video data acquired in step 202. The extracted audio is stored to memory 104. Processor 102 can use one or more programs, such as one or more programs of video processing module 120, to extract audio data from the video data. In some examples, processor 102 can execute one or more programs stored on memory 104 to identify which portions of the audio data in which the individual is speaking and trim the audio data to include only those portions. Trimming the audio data can reduce the file size of the audio data, which can improve the ease with which steps 222 and/or 224 can be performed in some examples.

In step 222, processor 102 generates a second feature set based on the audio extracted in step 220. The features can be, for example, based on vocal pitch, intonation, inflection, sentences stress, or another audio element indicative of information conveyance. In at least some examples, the presence of pauses or the absence of speaking in the audio data can also convey information. For example, long pauses between words or the absence of speaking may indicate that the individual is anxious, bored, and/or distracted, among other options. Portions of the audio data that lack vocal frequency information (e.g., those that correspond to pauses or individual silence) can be interpreted in combination with features from portions of the audio data in which the individual is speaking to determine what information, if any, is conveyed by the lack of frequency information. Processor 102 can create one or more values and store the value or values to memory 104 as the second feature set. In examples where an identifier was assigned to the audio data in step 220, the identifier can also be assigned to the second feature set extracted from the audio data.

In some examples, the second feature set can be generated by first converting the audio data into an audio spectrogram and by subsequently extracting features from the audio spectrogram. The spectrogram can describe, for example, amplitude or frequency ranges of the audio data. One or more programs, such as one or more computer-implemented machine learning models, can then be used to generate the second feature set from the spectrogram. In some examples, identifying features from an audio spectrogram of the audio data improves the accuracy of the features identified and stored in the second feature set.

The features extracted in step 222 can also relate to aspects of the individual's identity, such as physical attributes of the individual, the individual's physical environment, and/or the individual's physical location, among other examples. The features that relate to the individual's identity can be stored to the first feature set for use with step 240 of method 200 and, in some examples, can be labeled such that they are distinguished from features that relate to information conveyed by the individual suitable for predicting mental state.

In step 230, processor 102 extracts semantic text data. The semantic text data can be extracted from the audio data extracted in step 220 or from the video data acquired in step 202. As described previously, semantic text data refers to data that represents spoken words, phrases, sentences, and other sounds produced by the individual as readable text. The semantic text data can be, for example, a transcript of the words spoken in the audio portion of the video data. The semantic text data can be extracted from the audio data using one or more programs, such as a text-to-speech program.

In some examples, the video data acquired in step 202 can contain a text transcript of the words spoken by the individual. For example, if the video data is acquired from a video conferencing platform, the videoconferencing platform may embed a text transcript in the video data. In these examples, the semantic text data can be directly extracted from the video data rather than from the extracted audio data.

In step 232, processor 102 generates a third feature set based on the semantic text data extracted in step 230. The third feature set describes information conveyed by the words spoken by the individual semantic text data. Processor 102 can use one or more programs to generate the third feature set. In some examples, a computer-implemented machine learning model, such as a natural language understanding algorithm, can be used to generate the third feature set. The machine learning model can be configured to inspect the semantic text data for features related to the conveyance of information. The features can be, for example, phonemes, words, phrases, sentences, or other units of language that convey information and are stored in the semantic text data. The features can also be, for example, an intent and/or an entity in the semantic text data. A classifiable intent can include, for example, the intended meaning of a semantic text phrase. A classifiable entity can include, for example, words, phrases, sentences, or other units of language that provide additional context to further describe or classify an intent. In some examples, the machine learning model can compare the semantic text transcript of the individual to a library of vectorized text data to determine the content of the semantic text data. Processor 102 can then create one or more values that describe the information conveyed by the features and store the value or values to memory 104 as the third feature set. In examples where an identifier was assigned to semantic text data in step 230, the identifier can also be assigned to the third feature set.

The features of the third feature set can also relate to aspects of the individual's identity, such as physical attributes of the individual, the individual's physical environment, and/or the individual's physical location, among other examples. The features that relate to the individual's identity can be stored to the first feature set for use with step 240 of method 200 and, in some examples, can be labeled such that they are distinguished from features that relate to information conveyed by the individual suitable for predicting mental state.

In some examples, steps 210, 220, and 232 can be performed by video processing module 120 and steps 212, 222, and 232 can be performed by feature extraction module 130. In other examples, steps 210-212, 220-222, and 230-232 can be performed by three separate modules or sets of modules, such that each of the image, audio, and semantic text data are processed by separate modules stored on memory 104.

In step 240, processor 102 ensembles the individual's identity according to features extracted in steps 212, 222, and/or 232. Step 240 is optional and generates an identity that can be associated with the mental state in step 242.

The individual's identity can be ensembled by, for example, cross-referencing features of the first, second, and/or third feature sets with a table or array that relates features from image, audio, and/or text data to identity. In other examples, step 240 can be performed using a machine learning model trained to identify an individual based on a training set of features from image, audio, and/or semantic text data. In these examples, the identity ensembled in step 240 can include, for example, descriptions of the name, title, or organizational position of the individual, among other options. Additionally and/or alternatively, the identity generated in step 240 can include descriptions of the physical appearance, setting, built environment, or geographic location of the individual, among other options.

Following step 240, the first set of features, the second set of features, and the third set of features for each individual is associated with an ensembled identity for the individual. The identity of the individual can then be assigned to the mental state predicted for the individual in step 242.

In step 242, processor 102 predicts individual mental state based on the first, second, and/or third feature sets generated in steps 212, 222, and 232. Processor 102 uses a multidimensional mental state model, such as multidimensional mental state model 170 or multidimensional mental state model 300 (discussed subsequently with respect to FIG. 3), to predict individual mental state. Each dimension of the multidimensional mental state model corresponds to a different type of information conveyed by the video data acquired in step 202, such as intensity of mental state, pleasantness of mental state, whether the individual is conveying information the individual believes is important, the positivity of the information the individual is conveying, and/or the subject of the conversation in which the individual is participating (e.g., whether the subject is administrative, technical, etc.), among other options. Different regions of the multidimensional mental state model correspond to different mental states, allowing different combinations of dimensional values to represent different mental states. For example, in a two-dimensional mental state model in which one dimension corresponds to intensity of mental state and a second dimension corresponds to pleasantness of mental state (e.g., mental state model 170 shown in FIG. 4), two mental states can have similar values along the intensity dimension but different values along the pleasantness dimension. The mental states that correspond to each region of the multidimensional mental state model can be stored to memory 104 and recalled by processor 102 for use with step 242. Additionally and/or alternatively, one or more dimensions of the multidimensional mental state model can correspond to different mental states, as described previously with respect to multidimensional mental state model 170.

To predict mental state, processor 102 generates values for each dimension of the multidimensional mental state model based on the first, second, and/or third feature sets extracted in steps 212, 222, and 232, respectively. Processor 102 is then able to generate an overall individual mental state in step 242 by plotting the dimensional values in the multidimensional mental state model to determine what region of the multidimensional mental state model corresponds to the individual's mental state. The mental state that corresponds to that region of the multidimensional mental state model is the predicted mental state for the individual.

One or more computer-implemented machine learning models can be used to generate the individual mental state in step 242. One machine learning model can be used to determine the dimensional values for all dimensions of the multidimensional mental state model. Alternatively, multiple machine learning models can be used to determine dimensional values. For example, one computer-implemented machine learning model can be used to determine the dimensional value for each dimension. Advantageously, using separate computer-implemented machine learning models for each dimension of the multidimensional mental state model allows the first, second, and third feature sets to be weighed differently for different dimensions of the multidimensional mental state model.

Figure 3:
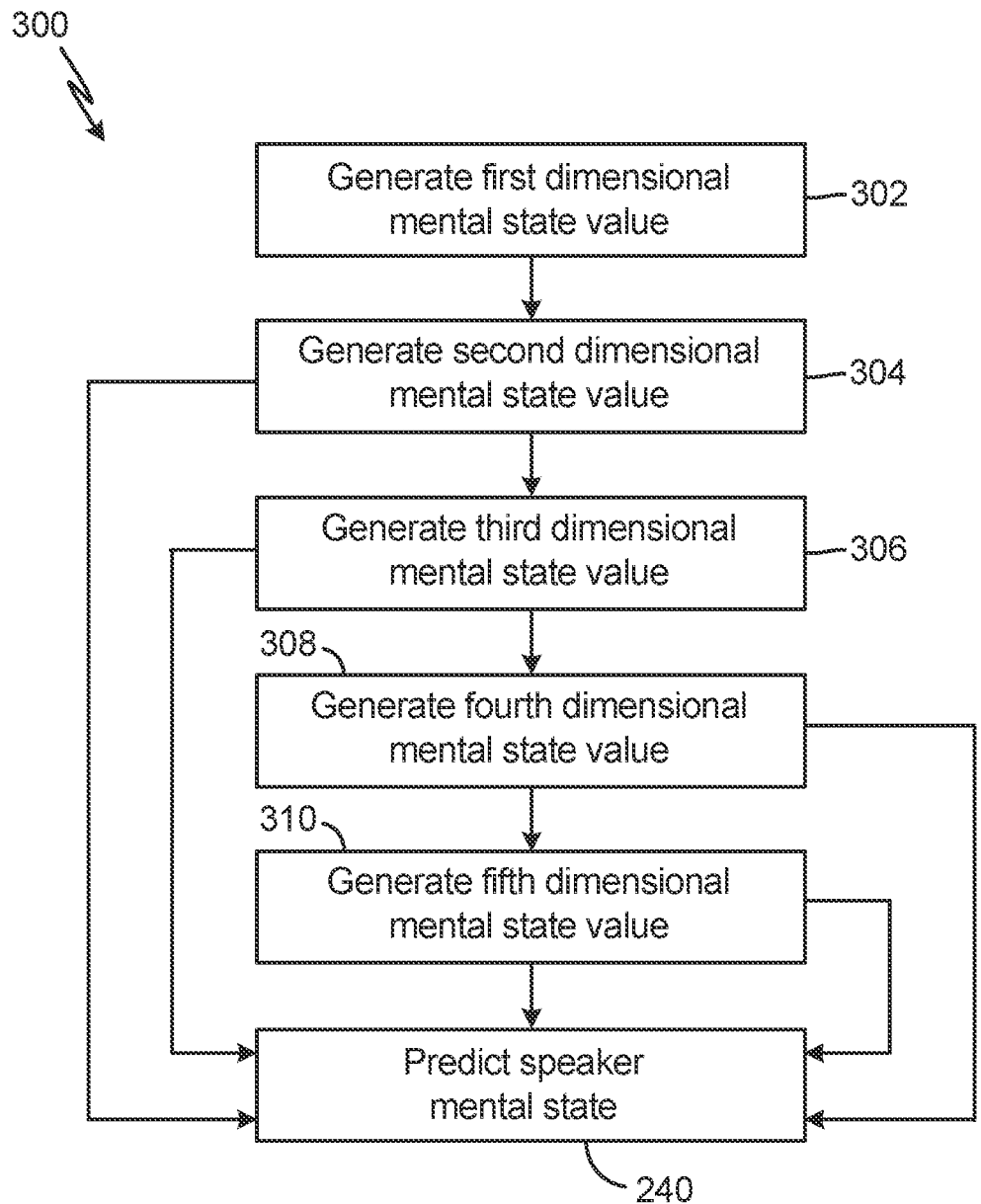
FIG. 3 is a flow diagram of an example of an example of a method of using a multidimensional mental state model to predict mental state suitable for use with the method of FIG. 2.

FIG. 3 is a flow diagram of method 300, which is a method of using a multidimensional mental state model to predict mental state. Method 300 is an example of a method of using extracted features to generate a mental state prediction according to step 242 of method 200. Method 300 includes steps of determining a first dimensional value for a first dimension of a multidimensional mental state model (step 302), determining a second dimensional value for a second dimension of a multidimensional mental state model (step 304), determining a third dimensional value for a third dimension of a multidimensional mental state model (step 306), determining a fourth dimensional value for a fourth dimension of a multidimensional mental state model (step 308), determining a fifth dimensional value for a fifth dimension of a multidimensional mental state model (step 310), and predicting an individual mental state (step 312).

In step 302, a first dimensional value is determined for a first dimension of a multidimensional mental state model. The first dimensional value is a value along the first dimension and is determined from the first feature set extracted in step 212 of method 200, the second feature set extracted in step 222 of method 200, and/or the third feature set extracted in step 232 of method 200. The features used to generate the first dimensional value are determined according to their predictive power to accurately determine values along the first dimension of the multidimensional state model. Step 302 can be performed using a computer-implemented machine learning model trained to associate a value in the first dimension of the multidimensional mental state model with features from the first, second, and/or third feature sets.

In step 304, a second dimensional value is determined for a second dimension of the multidimensional mental state model. The second dimensional value is a value along the second dimension and is determined from the first feature set extracted in step 212 of method 200, the second feature set extracted in step 222 of method 200, and/or the third feature set extracted in step 232 of method 200. Step 304 can be performed using a computer-implemented machine learning model trained to associate a value in the second dimension of the multidimensional mental state model with features from the first, second, and/or third feature sets.

The first and second dimensions describe any suitable aspect of or factor contributing to individual mental state. For example, the first and second dimensions can each describe intensity of mental state, pleasantness of mental state, whether the individual is conveying information the individual believes is important, the positivity of the information the individual is conveying, or the subject of the conversation in which the individual is participating (e.g., whether the subject is administrative, technical, etc.), among other options. Notably, the first and second dimensions describe different aspects of or factors contributing to individual mental state. Requiring that the first and second dimensions be different increases the granularity of and accuracy of predictions made with the multidimensional mental state model.

In some examples, the multidimensional mental state model includes only two dimensions. In these examples, method 300 proceeds to step 312 following step 304. In step 312, the first and second dimensional values are used to determine the individual's mental state according to the multidimensional mental state model. As described previously, different regions of the multidimensional mental state model can be assigned to different individual mental states, and the individual's mental state can be assigned according to the region in which a point lies having the first and second dimensional values.

In examples in which the multidimensional mental state model has additional dimensions, additional dimensional values can be generated and used in step 312. In the depicted example, where the multidimensional mental state model includes three dimensions, step 306 can be performed prior to step 312 to generate a third dimensional value corresponding to the third dimension. Where the multidimensional mental state model includes four dimensions, step 308 can be performed in addition to steps 302-306 prior to step 312 to generate a fourth dimensional value corresponding to the fourth dimension. Moreover, where the multidimensional mental state model includes five dimensions, step 310 can be performed in addition to steps 302-308 prior to step 312 to generate a fifth dimensional value corresponding to the fifth dimension.

Each of steps 306-310 can be performed in substantially the same way as steps 302 and 304 described previously. Notably, where the multidimensional mental state model includes more than two dimensions, each additional dimension represents a different aspect of or factor contributing to individual mental state than the first and second dimensions. Each of steps 306-310 can also be performed using computer-implemented machine learning models trained to associate features of the first, second, and/or third feature set with each additional dimension of the multidimensional mental state model. Having each dimension of the multidimensional mental state model represent a different aspect of or factor contributing to individual mental state advantageously increases the accuracy and granularity of the multidimensional mental state model, as will be explained in more detail subsequently.

As will be described in more detail subsequently, additional dimensions can be added to the multidimensional mental state model to provide improved resolution where needed to differentiate complex and similar mental states. As such, method 300 provides a flexible and scalable method that can be applied to a variety of multidimensional mental state models.

Figure 4:
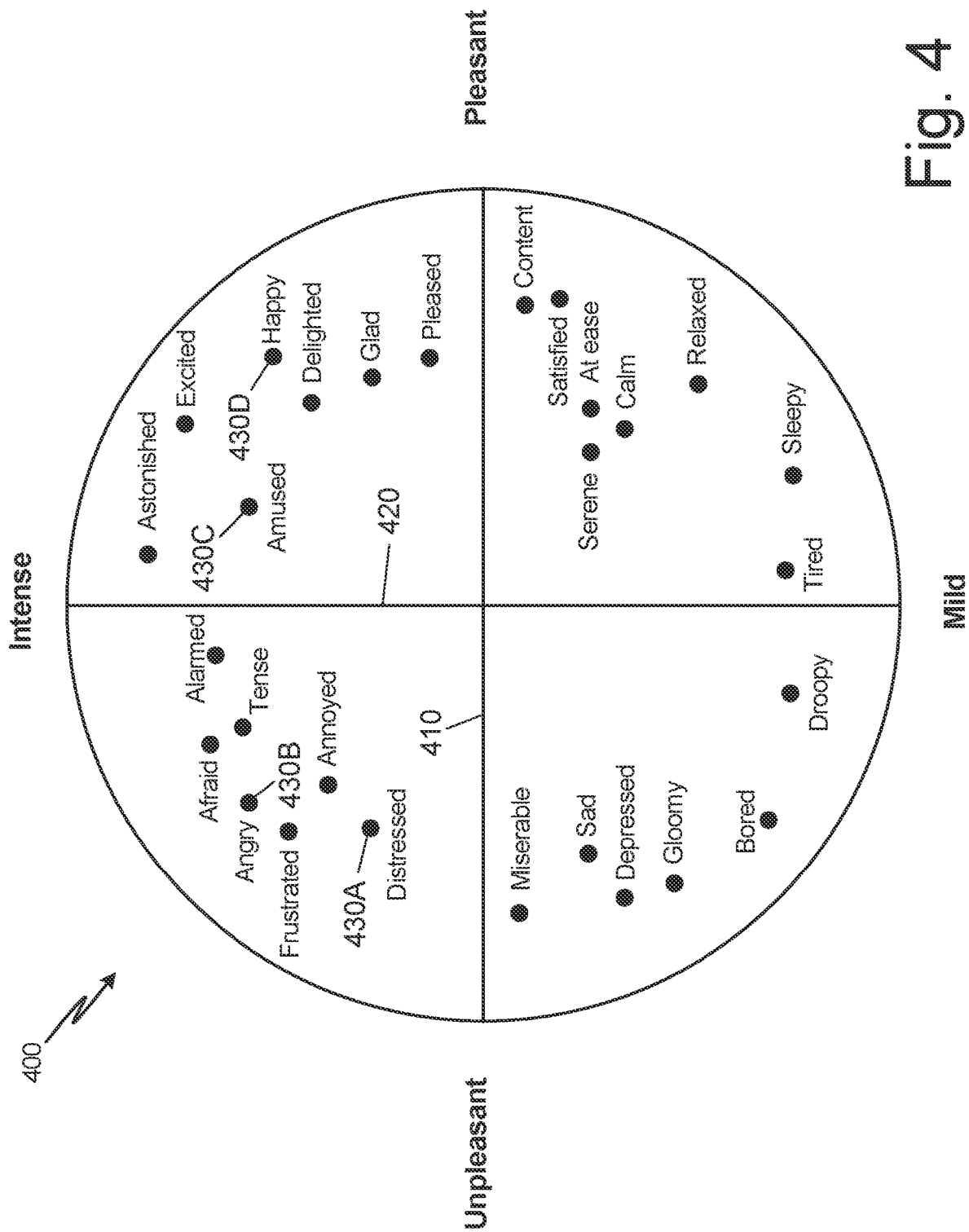
FIG. 4 is a schematic diagram of an example of a multidimensional mental state model.

FIG. 4 is a schematic diagram of multidimensional mental state model 400, which is an example of a multidimensional mental state model suitable for use in step 242 of method 200. Multidimensional mental state model is annotated with points corresponding to specific mental states and provides an example of how mental state predictions made using multidimensional mental state models allow for improved predictions over conventional methods of predicting mental state.

Multidimensional mental state model 400 is a two-dimensional mental state model and includes first dimension 410, second dimension 420, first mental state 430A, second mental state 430B, third mental state 430C, and fourth mental state 430D. In the depicted example, first dimension 410 describes the pleasantness of the individual's mental state. A low or negative value along first dimension 410 corresponds to an unpleasant mental state, while a high or positive value along first dimension 410 corresponds to a pleasant mental state. Second dimension 420 describes the intensity of the individual's mental state. A low or negative value along second dimension 420 corresponds to a mild or non-intense mental state, while a high or positive value along second dimension 420 corresponds to an intense mental state.

According to multidimensional mental state model 400, different individual mental states can be assigned various values relating to pleasantness and intensity of the mental state. For example, the individual's mental state can be both intense and unpleasant (e.g., afraid), mild and unpleasant (e.g., bored), pleasant and mild (e.g., relaxed), and/or intense and pleasant (e.g., happy).

By including multiple dimensions, multidimensional mental state model 400 can distinguish between mental states that have similar intensities but are dissimilarly pleasant, and between mental states that are similarly pleasant but that have different intensities. For example, multidimensional mental state model can distinguish between, for example, excitement and satisfaction, between alarm and astonishment, between distress and sadness, and between boredom and relaxation.

Further, multidimensional mental state model 400 can more clearly distinguish between mental states having generally similar pleasantness and intensities as compared to existing methods, which use, at most, a single dimension to distinguish between different mental states. Many existing methods of analyzing mental state attempt to identify mental state based only on the presence or absence of features associated with a particular mental state. Where a model is used to analyze mental state, existing methods use a model that contains at most a single dimension, with different mental states ordered along the single dimension of mental state.

Advantageously, the use of a multidimensional mental state model can allow for significant improvements in resolution between similar mental states, which significantly improves the accuracy of predictions made using the multidimensional mental state model. For example, points 330A and 330B, which correspond to "distressed" and "angry" mental states, respectively, are difficult to resolve by pleasantness alone due to their similar pleasantness values. However, points 330A and 330B can be resolved by their intensity values, which are more dissimilar than the pleasantness values for points 430A and 430B. Similarly, points 430C and 430D, which correspond to "happy" and "amused" mental states, respectively, are difficult to resolve based on their intensity values. However, points 430C and 430D can also be resolved according to their pleasantness values, which are more dissimilar than their intensity values.

These examples highlight the manner in which multidimensional mental state model 400 provides improved granularity and resolution of mental state as compared to existing models. As multidimensional mental state model 400 is able to more clearly distinguish between mental states having similar values along one dimension, multidimensional mental state model 400 is also able to represent a more complex set of mental states than existing mental state models using a single-dimension. Further, the inclusion of multiple dimensions significantly improves the resolution of multidimensional mental state model 400 by more clearly differentiating between different mental states than existing models. The improved resolution of multidimensional mental state model 400 allows for significantly more accurate predictions of mental state than existing models.

Adding additional dimensions to multidimensional mental state model 400 can allow nearby or similar mental states to be further distinguished. For example, additional dimensions describing information importance, information positivity, and/or the subject of the information (i.e., whether the information is administrative, technical, etc.) can further be used to resolve and distinguish between similar overall mental states. In examples where each dimension of the multidimensional mental state model represents a separate mental state (e.g., one or more of confusion, envy, calmness, sleepiness, etc.), the inclusion of additional dimensions can also allow for more accurate description of an individual's mental state. For example, a three-dimensional mental state model can describe three separate mental states that an individual may be experiencing simultaneously and that contribute to the individual's overall mental state. Similarly, a four-dimensional mental state model can describe four separate mental states and a five-dimensional mental state model can describe five separate mental states. Other examples of mental state models with more than five dimensions are contemplated herein.

Advantageously, generating an individual mental state with a multidimensional mental state model, such as multidimensional mental state model 170 or 400, allows for more accurate predictions of individual mental state. Specifically, use of a multidimensional mental state model allows for different mental states, components of mental states, factors that contribute to an individual's mental state, and aspects of communicated information (e.g., intensity, pleasantness, positivity, importance of discussion, etc.) to be determined individually. The selected dimensions of mental state are combined to provide a significantly more accurate prediction of individual mental state than conventional methods. For example, the features derived from audio, image, and semantic text can be weighed differently in different dimensions of the multidimensional mental state model, improving the accuracy of the model as compared to conventional methods. Features from each type of data can be weighed according to their predictive power for each dimension, improving the accuracy with which each dimension of mental state can be determined and, thereby, increasing the accuracy of the overall mental state prediction made using the multidimensional model.

Additionally and/or alternatively, for some dimensions, portions of the video (e.g., image, audio, or semantic text data) can excluded entirely from the calculation of dimensional values of the individual mental state. For example, features from the first and second feature sets (corresponding to image and audio data, respectively) can be used to determine values in the first and second dimensions, and the third feature set (corresponding to semantic text) can be used to determine values in the third dimension. In other examples, all three information feature sets can be used to determine a single dimension.

Further, the use of a multidimensional mental state model also increases the granularity with which individual mental state can be determined. Additional dimensions can be added to the multidimensional mental state model as required for a given application. As each dimension can be determined with different weights assigned to and/or with different combinations of image, audio, and semantic text data, as described previously, increasing the number of dimensions of the multidimensional mental state model also increases the number of individual mental states described by the multidimensional mental state model, improving the resolution of the model and allowing for more accurate mental state predictions.

The use of different combinations of the three types of information present in video data (i.e., image, audio, and semantic text) can provide further advantages and improvements to both the efficiency and accuracy of the multidimensional mental state model. More specifically, excluding different combinations of image, audio, and text data allows non-predictive information to be disregarded for calculation of a dimensional value for a given dimension of the multidimensional mental state model, simultaneously improving the efficiency and accuracy with which mental state is determined. For example, where a multidimensional model includes a dimension for discussion importance, text data may offer significantly more insight into the importance of a particular discussion than image or audio data. The multidimensional mental state model can be configured so that only features from the third feature set generated in step 232 of method 200 (i.e., those extracted from the text data) are used to calculate the dimension associated with discussion importance, improving accuracy by disregarding non-predictive data and, consequently, improving efficiency by only requiring one type of data to calculate the dimensional value for the discussion importance dimension.

Returning to method 200, steps 246-250 relate to presentation of the identity generated in step 240 and/or the mental state information predicted in step 242. Steps 246-250 are optional and are not required to produce an individual mental state prediction. Steps 246-250 can be performed by video reconstruction module 164 or another suitable software module.

In step 246, processor 102 enhances the images extracted in step 204 and/or the audio extract in step 220 based on the predicted individual mental state generated in step 242. The enhancements applied in step 246 are chosen to emphasize the predicted individual mental state generated in step 242. For example, if the predicted mental state is "anger" or a similar mental state, the images and audio can be enhanced to more clearly demonstrate that the individual is angry. As a further example, if the predicted mental state is "confusion," the images and audio can be enhanced to more clearly demonstrate that the individual is confused. Processor 102 can enhance images by, for example, altering one or more aspects of the image data. Processor 102 can be configured to alter the color of the background of the image data, to add additional image data to portions of the image data corresponding to the individual (e.g., by adding picture or symbol data that represents the individual mental state). Processor 102 can enhance the audio data by altering or augmenting one or more portions of the audio data. For example, processor 102 can be configured to apply a vocal effect or audio filter (e.g., delay, distortion, echo, pitch shift, pitch quantization, etc.) based on the individual's predicted mental state.

In step 248, processor 102 reconstructs the video data by combining the enhanced images and enhanced audio generated in step 246. The enhanced video is output in step 250 to a user interface, such as a display or audio device. The output video can be displayed to other users in addition to or place of the original video data acquired in step 202. Where the individual is, for example, videoconferencing with other users, the enhanced video can be output through the videoconferencing software to visually and/or aurally communicate the individual's mental state to other members of the videoconference. The other users are able to observe the enhanced video and, if desired, adjust their interaction with the individual appropriately. Where the videoconference software offers a video preview, the enhanced video can also be output to the video preview to the individual. The individual can then, if desired, adjust their body language, vocal tone, and language to alter their mental state, which can be displayed in a new enhanced video signal following subsequent iterations of method 200.

In other examples, individual state of mind can be presented in means other than through enhanced video data generated in steps 246-250. For example, processor 102 can additionally and/or alternatively generate a report describing the individual's state of mind predicted in step 242. The report can be cumulative, for example, and can be presented to the individual after the individual is no longer speaking, videoconferencing, presenting, and/or otherwise conversationally engaged with other individuals.

Advantageously, method 200 allows prediction of mental state based solely on video data of an individual rather than on biometric measurements or other more invasive measurement techniques. Further, as method 200 uses a multidimensional mental state model, the advantages of which are outlined in detail previously and particularly with respect to step 242, method 200 provides numerous advantages over existing models of mental state. Particularly, the multidimensional mental state models used by method 200 are scalable and can include any number of dimensions based on operational need. The dimensions can advantageously include any combination of mental states, mental state components, factors that contribute to mental state, and aspects of communicated information.

Method 200 provides benefits to accessibility for individuals having perception impairments, such as impairments to speech or vision. Perception-impaired people can experience difficulty in reading facial expressions or understanding emotions expressed in speech. Method 200 enables the display of a machine-generated mental state prediction that can be displayed or otherwise communicated to an individual with a hearing-, vision-, and/or perception impairment to improve understanding of information conveyed by other individuals with which they are interacting.

As described previously, method 200 can be iterated in time-based intervals over the course of an interaction captured by video. Advantageously, the use of computer-implemented machine learning models enables method 200 to with very short time intervals between iterations, such that method 200 is performed in real-time or substantially in real-time. Where method 200 is performed in real-time or substantially in real-time, the predicted mental states created using method 200 can be presented in real-time or substantially real-time, improving understanding for individuals with and without perception impairments and enabling individuals to act on an individual's predicted mental state in real-time or in substantially real-time.

While method 200 has been described herein with respect to mental state prediction for a single individual, in other examples, method 200 can be adapted to determine mental state for multiple individuals. Where there is video data (e.g., video data 110A-N) for each individual that depicts each individual separately and without other individuals, method 200 can be performed sequentially, simultaneously, or substantially simultaneously for each video data to predict mental state for each individual.

In examples where the video data acquired in step 102 (e.g. video data 110A-N) depicts more than one individual, features can be extracted for each individual and mental state can be predicted for each individual based on the features associated with the individual.

In these examples, the images obtained from the video data can be cropped by processor 102 to create sets of still images for each individual captured by the video data. Processor 102 can use one or more programs stored to memory 104 to identify individuals in the image data. The one or more programs can be, for example, one or more machine learning models, such as one or more computer vision models. The cropped image data for each individual can be assigned an identifier that can be used to identify the features extracted from the cropped image data for each individual. The identifier can be, for example, a name, a number, or another suitable method of identifying the individual. The program used to identify an individual in image data can be, for example, a machine learning model, such as a computer vision model.

Similarly, the audio extracted in step 220 can be trimmed to create trimmed audio data for each individual. Processor 102 can execute one or more programs, such as one or more computer-implemented machine learning models, to identify individuals within the audio data and to trim the complete audio from the video data to create audio data for each individual. In some examples, individual diarization of the audio file can be performed to separate the audio corresponding to each individual. The trimmed audio of each individual can be assigned an identifier that can be used to subsequently identify features extracted from the trimmed audio for each individual. The identifier can be, for example, a name, a number, or another suitable method of identifying the individual among other individuals in the audio.

Semantic text data can be extracted in step 230 from the trimmed audio of each individual. Additionally and/or alternatively, where the video data includes an embedded transcript of semantic text data, semantic text data corresponding to each individual can be isolated using one or more programs, such as one or more computer-implemented machine learning models. Where the semantic text data extracted in step 230 is based on the audio data extracted in step 220, the identifier assigned to the audio data extracted in step 220 can also be assigned to the semantic text data to subsequently identify features extracted from the semantic text data for each individual. In other examples, an identifier for the semantic text data can be determined based on the contents of the semantic text data.

The image, audio, and semantic text data for each individual can be re-associated prior to performance of step 242 of method 200. In some examples, the image, audio, and semantic text data can be re-associated by performing step 240, ensembling an identity for the individual, for each set of image, audio, and semantic text data. For example, each of the image, audio, and/or semantic text data can be cross-referenced with a table or array that relates features from image, audio, and text data to identity. Additionally and/or alternatively, each of the image, audio, and semantic text data can be analyzed using a machine learning model trained to identify an individual based on a training set of features from image, audio, and semantic text data. The identities corresponding to each of the image, audio, and/or semantic text data can be used to re-associate the image, audio, and semantic text data for each individual. In examples where the semantic text data is extracted from audio data, the identity information obtained for the audio data can be used for the semantic text data and separate identity information does not need to be obtained for the semantic text data.

Where the video data acquired in step 202 is a video stream from a video conferencing platform, information from the video conferencing platform can be used to identify and re-associate image, audio, and semantic text information for each individual present in the video data. For example, text present in the image data describing a username or name of an individual can be identified by one or more programs executed by processor 102 and stored as the identifier for the image data. Processor 102 can use one or more programs to identify which portions of the audio data and semantic text data correspond to the image data. For example, processor 102 can use one or more programs to identify timestamps during which the individual is speaking. The programs can identify, for example, which portions of the image data include mouth movements associated with speaking. Processor 102 can re-associate trimmed audio files with the image data based on the timestamp information. Similarly, processor 102 can re-associate semantic text information based on the timestamp information. For example, where the semantic text data is derived from the trimmed audio files, the image data associated with the trimmed audio can also be associated with the semantic text data. In examples where the video conferencing platform embeds semantic text data in the video data and further labels the semantic text data with the same username or name present in the image data, the semantic text data can also be associated by comparing the username or name present in the image and semantic text data.

As outlined herein, various methods can be used to scale method 200 for analyzing mental state for multiple individuals depicted in video data. Advantageously, this substantially increases the flexibility of method 200 to be applied to a wide variety of video data.

Figure 5:
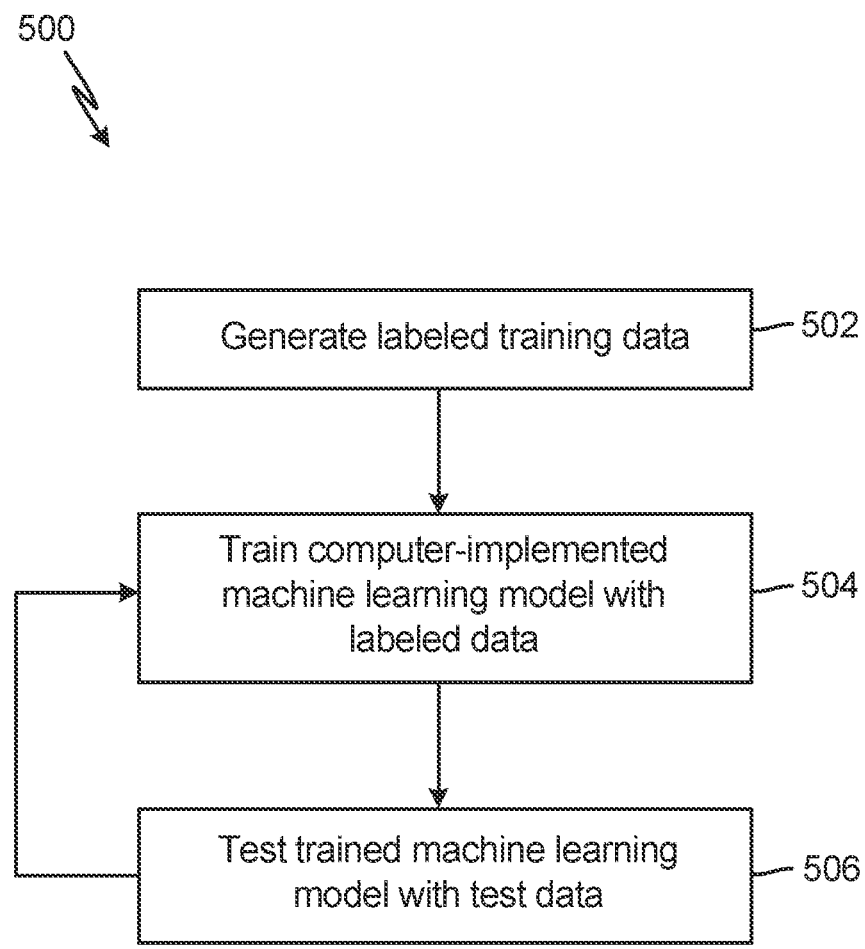
FIG. 5 is a flow diagram of an example of a method of training a computer-implemented machine learning model suitable for use with the methods of FIGS. 2-3.

FIG. 5 is a flow diagram of method 500, which is a method of training a computer-implemented machine learning model. Method 500 includes steps 502-506 of generating labeled training data (step 502), training the computer-implemented machine learning model with the labeled data (step 504), and testing the trained computer-implemented machine learning model with test data (step 506). Method 500 can be used to train any machine learning model described herein (e.g., for a machine learning model for the first dimensional mental state value, the second dimensional mental state value, the third dimensional mental state value, etc.), but will be discussed with respect to a generic machine learning model for explanatory purposes.

In step 502, labeled data is generated. The labeled data can be, for example, audio data, image data, semantic text data, or labeled outputs of another trained machine learning model. The data can be labeled according to the dimensions of the multidimensional mental state model used to predict mental state in step 242. For example, if the multidimensional mental state model used with method 200 includes intensity and pleasantness dimensions, the labeled data used in step 502 can be labeled to include intensity and pleasantness values. Further, if the type of data is used to determine a particular subset of dimensions of the multidimensional mental state model, the labeled data 502 can be labeled only values for those dimensions to improve model fit. For example, the multidimensional mental state model can include three dimensions of intensity, pleasantness, and importance, and audio data can be used to determine only values along the intensity and pleasantness dimensions. The labeled audio data used to train a machine learning model in step 502 can be labeled only with intensity and pleasantness values to improve fit of the machine learning model to the relevant intensity and pleasantness values with which the model is intended to be used.

In step 504, the labeled data is used to train the computer-implemented machine learning model. As used herein, "training" a computer-implemented machine learning model refers to any process by which parameters, hyper parameters, weights, and/or any other value related model accuracy are adjusted to improve the fit of the computer-implemented machine learning model to the training data.

In step 506, the trained computer-implemented machine learning model is tested with test data. The test data used in step 506 is unlabeled data that is used to qualify and/or quantify performance of the trained computer-implemented machine learning model. More specifically, a human or machine operator can evaluate the performance of the machine learning model by evaluating the fit of the model to the test data. Step 506 can be used to determine, for example, whether the machine learning model was overfit to the labeled data during model training in step 504.

As depicted in FIG. 5, steps 504 and 506 can be performed iteratively to improve the performance of the machine learning model. More specifically, if the fit of the model to the unlabeled data determined in step 506 is undesirable, step 504 can be repeated to further adjust the parameters, hyper parameters, weights, etc. of the model to improve the fit of the model to the test data. Step 506 can then be repeated with a new set of unlabeled test data to determine how the adjusted model fits the new set of unlabeled test data. If the fit continues to be undesirable, further iterations of steps 504 and 506 can be performed until the fit of the model becomes desirable.

The methods and systems disclosed herein advantageously allow for the training and use of a series of machine learning models that can predict the mental state of an individual captured in video data.

As described previously, the use of a multidimensional mental state model, such as multidimensional mental state model 400, provides significant advantages over existing methods of determining individual mental state, including existing methods that utilize multiple machine learning models and/or multiple types of data capturing the individual (e.g., image data, audio data, and/or text data). Specifically, a multidimensional mental state model according to the present disclosure improves the accuracy of mental state predictions and the efficiency with which mental state predictions can be computed. Further, a multidimensional mental state model provides significant flexibility over other existing mental state models and provides improved granularity and resolution, thereby further improving the accuracy of mental state predictions made using the multidimensional mental state model.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the present disclosure.

The invention claimed is:

1. A method of predicting individual mental state, the method comprising:
  extracting image data, audio data, and semantic text data from video data, wherein
    a first individual is portrayed in the video data;
  analyzing the image data to identify a first feature set;
  analyzing the audio data to identify a second feature set;
  analyzing the semantic text data to identify a third feature set;
  generating, by a first computer-implemented machine learning model, a first dimensional mental state value based on first features from at least one of the first feature set, the second feature set, and the third feature set, wherein the first dimensional mental state value describes a first dimension of a multidimensional mental state model;
  generating, by a second computer-implemented machine learning model, a second dimensional mental state value based on second features from at least one of the first feature set, the second feature set, and the third feature set, wherein the second dimensional mental state value describes a second dimension of the multidimensional mental state model;
  generating, by a third computer-implemented machine learning model, a third dimensional mental state value based on third features from at least one of the first feature set, the second feature set, and the third feature set, wherein the third dimensional mental state value describes a third dimension of the multidimensional mental state model;
  generating, by a fourth computer-implemented machine learning model, a fourth dimensional mental state value based on fourth features from at least one of the first feature set, the second feature set, and the third feature set, wherein the fourth dimensional mental state value describes a fourth dimension of the multidimensional mental state model;
  generating, by a fifth computer-implemented machine learning model, a fifth dimensional mental state value based on fifth features from at least one of the first feature set, the second feature set, and the third feature set, wherein the fifth dimensional mental state value describes a fifth dimension of the multidimensional mental state model;
  predicting a mental state for the individual based on the first dimensional mental state value, the second dimensional mental state value, the third dimensional mental state value, the fourth dimensional mental state value, the fifth dimensional mental state value, and the multidimensional mental state model, wherein:
    the first dimension of the multidimensional mental state model corresponds to an intensity of mental state,
    the second dimension of the multidimensional mental state model corresponds to a pleasantness of mental state,
    the third dimension of the multidimensional mental state model corresponds to an importance of discussed information, wherein the discussed information is information discussed by the individual in the semantic text data,
    the fourth dimension of the multidimensional mental state model corresponds to a positivity of the discussed information, and
    the fifth dimension of the multidimensional mental state model corresponds to a topic of the discussed information; and
  outputting the predicted mental state.

2. The method of claim 1, further comprising:
  augmenting a portion of the video data associated with the first individual based on the predicted mental state of the individual; and
  outputting the augmented video data.

3. The method of claim 1, wherein predicting the mental state for the individual based on the first dimensional mental state value, the second dimensional mental state value, the third dimensional mental state value, the fourth dimensional mental state value, the fifth dimensional mental state value, and the multidimensional mental state model comprises:
  identifying a region of the multidimensional mental state model that corresponds to a point having the first dimensional mental state value, the second dimensional mental state value, the third dimensional mental state value, the fourth dimensional mental state value, and the fifth dimensional mental state value; and
  identifying a mental state associated with the region.

4. The method of claim 1, wherein:
  the first dimensional mental state value is generated based on the first feature set and the second feature set; and
  the second dimensional mental state value is generated based on the first feature set and the second feature set.

5. The method of claim 4, wherein the third dimensional mental state value is generated based on the third feature set.

6. The method of claim 1, further comprising:
ensembling an identity of the individual based on one or more of first set of features, the second set of features, and the third set of features, wherein the ensembled identity can be used to identify the individual; and
outputting the ensembled identity with the predicted mental state.

7. The method of claim 1, wherein:
generating the first feature set comprises identifying, with a first computer-implemented machine learning model, classifiable features in the image data;
generating the second feature set comprises identifying, with a second computer-implemented machine learning model, classifiable features in the audio data; and
generating the third feature set comprises identifying, with a third computer-implemented machine learning model, classifiable features in the semantic text data.

8. The method of claim 1, wherein first feature set comprises one or more of:
a hand gesture;
head tilt;
an eyebrow position;
a mouth position;
a mouth shape;
a presence of eye contact;
an amount of eye blinking;
a speed of eye blinking; and
forehead wrinkling.

9. The method of claim 1, wherein the second feature set comprises one or more of cadence, vocal tone, vocal pitch, and vocal quaver.

10. A system for predicting individual mental state, the system comprising:
a processor;
a user interface configured to enable an operator to interact with the processor; and
a memory encoded with instructions that, when executed, cause the processor to:
extract image data, audio data, and semantic text data from video data, wherein a first individual is portrayed in the video data;
analyze the image data to identify a first feature set;
analyze the audio data to identify a second feature set;
analyze the semantic text data to identify a third feature set;
generate, by a first computer-implemented machine learning model, a first dimensional mental state value based on first features from at least one of the first feature set, the second feature set, and the third feature set, wherein the first dimensional mental state value describes a first dimension of a multidimensional mental state model;
generate, by a second computer-implemented machine learning model, a second dimensional mental state value based on second features from at least one of the first feature set, the second feature set, and the third feature set, wherein the second dimensional mental state value describes a second dimension of the multidimensional mental state model;
generate, by a third computer-implemented machine learning model, a third dimensional mental state value based on third features from at least one of the first feature set, the second feature set, and the third feature set, wherein the third dimensional mental state value describes a third dimension of the multidimensional mental state model;
generate, by a fourth computer-implemented machine learning model, a fourth dimensional mental state value based on fourth features from at least one of the first feature set, the second feature set, and the third feature set, wherein the fourth dimensional mental state value describes a fourth dimension of the multidimensional mental state model;
generate, by a fifth computer-implemented machine learning model, a fifth dimensional mental state value based on fifth features from at least one of the first feature set, the second feature set, and the third feature set, wherein the fifth dimensional mental state value describes a fifth dimension of the multi-dimensional mental state model;
predict a mental state for the individual based on the first dimensional mental state value, the second dimensional mental state value, the third dimensional mental state value, the fourth dimensional mental state value, the fifth dimensional mental state value, and the multidimensional mental state model, wherein:
the first dimension of the multidimensional mental state model corresponds to an intensity of mental state,
the second dimension of the multidimensional mental state model corresponds to a pleasantness of mental state,
the third dimension of the multidimensional mental state model corresponds to an importance of discussed information, wherein the discussed information is information discussed by the individual in the semantic text data,
the fourth dimension of the multidimensional mental state model corresponds to a positivity of the discussed information, and
the fifth dimension of the multidimensional mental state model corresponds to a topic of the discussed information; and
output the predicted mental state.

* * * * *